United States Patent [19]

Heidlas et al.

[11] Patent Number: 5,789,647
[45] Date of Patent: Aug. 4, 1998

[54] PROCESS FOR THE EXTRACTION OF NATURAL CAROTENOID DYES

[75] Inventors: Jürgen Heidlas, Trostberg; Jan Cully; Johann Wiesmüller, both of Garching; Heinz-Rüdiger Vollbrecht, Altenmarkt, all of Germany

[73] Assignee: SKW Trostberg Aktiengesellschaft, Trostberg, Germany

[21] Appl. No.: 793,180

[22] PCT Filed: Aug. 18, 1995

[86] PCT No.: PCT/EP95/03298

§ 371 Date: Feb. 19, 1997

§ 102(e) Date: Feb. 19, 1997

[87] PCT Pub. No.: WO96/06138

PCT Pub. Date: Feb. 29, 1996

[30] Foreign Application Priority Data

Aug. 18, 1994 [DE] Germany ............... 44 29 506.5

[51] Int. Cl.$^6$ ................ C07C 7/00; C07C 403/00
[52] U.S. Cl. ................ 585/833; 585/803; 585/351; 585/867

[58] Field of Search .................. 585/803, 351, 585/833, 867

[56] References Cited

U.S. PATENT DOCUMENTS

| 4,345,976 | 8/1982 | Peter et al. ............... 203/49 |
| 5,310,554 | 5/1994 | Haigh et al. .............. 424/429 |

FOREIGN PATENT DOCUMENTS

| 0480476 | 4/1992 | European Pat. Off. |
| 3114593 | 12/1982 | Germany. |
| 60176563 | 9/1985 | Japan. |

*Primary Examiner*—Walter D. Griffin
*Assistant Examiner*—Nadine Preisch
*Attorney, Agent, or Firm*—Felfe & Lynch

[57] ABSTRACT

A process for the extraction of carotenoid dyes from pre-dried natural starting materials is described using compressed gases such as propane and/or butane in which organic entraining agents can be additionally added in order to facilitate and complete the extraction process. With the aid of this process highly concentrated carotenoid dyes are obtained in high yield.

18 Claims, No Drawings

PROCESS FOR THE EXTRACTION OF NATURAL CAROTENOID DYES

BACKGROUND OF THE INVENTION

The present invention concerns a process for the extraction of carotenoid dyes from natural starting materials using compressed gases.

Carotenoids are yellow to deep-red coloured polyene dyes which are widespread in the plant and animal kingdom. Their colour is based on a tetraterpenoid structure with conjugated double bonds. The carotenoids are differentiated according to their functional groups into carotenes (pure hydrocarbons) and xanthophylls (having polar substituents on the carbon skeleton). The obsolete term "lipochromes" takes into account the liposoluble properties of these dyes.

The food industry has traditionally made use of their strong colouring action and their manifold applications. Although carotenoids are widespread in nature, industry was for a long time not sufficiently able to exploit productive sources from which larger quantities of carotenoids could be obtained commercially. The methods of the synthetic chemical industry were the first to lead to the production of synthetic carotenoids in lower cost ranges.

The increasingly more critical conduct of consumers and the resulting demand for "natural" foods and dyes has now set the task for the modern food technology to provide food additives that are derived form natural sources and have furthermore been processed mildly and naturally. Fermenting processes have recently enabled carotenoids to be obtained microbiologically and thus naturally and in large amounts.

A wide variety of processes have been developed in the past for the isolation of carotenoid dyes from natural sources. Thus for example the U.S. Pat. No. 2,170,872 describes a method for the extraction of carotenoids in which the plant material is treated with sodium hydroxide solution in order to break up the fat-soluble matrix components, it is then heated with steam and finally extracted with petroleum ether or hexane. Subsequently the extract obtained in this way has to be distilled with steam and the aqueous phase has to be extracted again with an oil. The oily solution that is formed is used as a colourant.

The use of organic solvents is still widespread in order to obtain carotenoids in larger amounts starting from dried natural products. Such a method is described in the U.S. Pat. No. 1,988,031 according to which plant material, in particular carrots, is firstly admixed with lipophilic solvents such as propyl alcohol in order to precipitate the carotenoid dyes in this manner. The carrot powder obtained in this way is subsequently repeatedly extracted with petroleum ether and concentrated during which the carotenoid dyes crystallize more and more.

WO 92/18 471 offers a solvent-free process. In this process the extract derived from plant material is separated into a liquid fraction containing carotenoids and into a pulp and the liquid fraction is admixed with salts such as $CaCl_2$ which precipitates the carotenoids.

However, in principle it has proven to be advantageous to remove accompanying fatty substances during the extraction of carotenoids which would otherwise pass into the extract and subsequently,—in particular at low carotenoid concentrations,—impair crystallization of the dyes. Due to this experience a procedure has often been used in which the interfering oils are saponified such as for example according to U.S. Pat. No. 2,032,006. The process described there utilizes the finding already described by Preston et al. (Food Chem. 5(1), 47, 1980) that high process temperatures should be avoided when isolating carotenoids, since these compounds are very thermolabile and tend to isomerize their double bonds and/or decompose at high temperatures.

The rapid development of the extraction of natural substances with the aid of for example compressed gases has enabled carotenoid dyes to be isolated under milder processing conditions than those described above. Thus in U.S. Pat. No. 4,400,398 an extraction method is described with supercritical $CO_2$ that proceeds in several steps in which aromatic compounds (peppery substances) are firstly separated from red pepper and the loaded supercritical gas is then purified in order to finally re-use it for dye extraction; the pressures in the dye extraction step are >350 bar.

The processing parameters which are generally necessary for dye extraction with supercritical $CO_2$ such as very high pressures (up to 700 bar) and extremely high specific gas flow rates yield only very unsatisfactory results with regard to the isolation of carotenoid dyes which is why the use Of $CO_2$ extraction for isolating dyes has proven to be uneconomical.

A newer extraction method described in the U.S. Pat. No. 5,264,212 likewise utilizes supercritical $CO_2$. However, circumvents the high pressures that are usually necessary for the extraction of carotenoids by extracting the undesired accompanying substances from red pepper but not the dyes, leaving the dyes in the starting material. The serious disadvantage of this method is, however, that carotenoid dyes with only a very low purity are obtained in this way since the greater part of the complex natural substance matrix remains in the residue together with the dyes.

Thus the described disadvantages of the state of the art have posed the problem of providing an improved process for the extraction of carotenoid dyes in a technical and economical sense which enables carotenoids to be isolated in high concentrations and at the same time in high yield.

THE INVENTION

This object was achieved by a process for the extraction of carotenoid dyes from natural starting compounds using compressed gases which is characterized in that the pre-dried starting material is extracted with compressed propane and/or compressed butane, if desired in the presence of an organic entraining agent, at temperatures between 20° and 100° C. and pressures between 10 and 200 bar.

Despite the known good dissolving capacity of compressed propane and compressed butane for lipophilic substances it surprisingly turned out that the solubility of large amounts of carotenoid dyes in both the said gases or mixtures thereof is significantly increased when an organic entraining agent is additionally used as cosolvent. This is even more surprising since the sum of the individual dissolving capacities of the entraining agents that come into consideration and of the solvents propane and butane would have led one to expect significantly poorer total dissolving capacities than the actual mixture of these solvents in fact exhibited.

On the other hand it would not have been expected that the extraction of natural substances with low carotenoid contents proceeds nearly quantitatively in the selected, sometimes very high, temperature ranges even without addition of organic entraining agents.

In order to carry out the present invention it has proven to be expedient to pre-dry the respective starting material of animal, plant or microbial origin to a water content of <80% by weight according to the prior art in which a water content of <50% by weight is to be preferred. The best extraction results can be obtained using an extremely dry extraction material with water contents of <10% by weight. Natural plant products such as paprika, carrots, citrus fruit peelings or certain parts of flowers such as tagetes blossoms which are first dried and then pulverized and/or pelleted have proven to be particularly suitable as starting materials. Dried parts of crustaceans are particularly recommended as animal sources.

Especially in the case of starting materials with high contents of carotenoid dyes such as e.g. appropriate fermentation residues it is an important feature of the invention that the extraction is carried out in the presence of an organic entraining agent. Solvents should be selected for this purpose which, in accordance with the directives of the EC commission 88/344/CEE (official journal of the European Community No. L 157/28 of 24.06.1988), are suitable for use in food technology without restriction as solvents of group 1. In this connection it is preferable to select a member from the series acetone, ethyl acetate, butyl acetate and ethanol—in addition to the actual inventive solvents propane and butane—however, according to the present invention other short-chained alcohols with 1 to 5 carbon atoms, preferably methanol but also butanols, petroleum ether and other pure hydrocarbons such as hexane can also be used.

The selected concentration for this purpose of the entraining agent that is fed in can be varied within relatively wide ranges and has to be matched to the respective natural substances to be extracted. Technical considerations dictate that the amounts of entraining agent that are fed in are kept as low as possible and that at the same time the specific solvent flow-rate is kept near the minimum. Taking into consideration these stipulations, concentrations of entraining agents of between 5 and 50% by weight relative to the amount of compressed gas (mixture) being present in the extractor have proven to be suitable for the present process, and consideration of economic aspects would suggest a preferred range of 10 to 30% by weight.

With regard to the process parameter pressure, it has proven to be advantageous in the extraction process according to the invention to use significantly lower pressures than those known for example from $CO_2$ extraction techniques. Thus although the extraction pressure of the present invention depends on the composition of the respective compressed gas(mixture), the pressures in the process are always within the preferred range between 15 and 40 bar in which the pressure can be <40 bar when using compressed propane and <20 bar for compressed butane. Of course higher process pressures can also be used, these are however, in the first instance not really necessary from a technical point of view and in the second instance for other reasons one always tries to keep the process pressure as low as possible.

The extraction temperatures are of course closely correlated to the stated pressures. Apart from the broad temperature range of 20° to 100° C. that is essential for the invention, it has proven to be very advantageous for effectively carrying out the process to preferably extract at temperatures between 50° and 90° C.

The actual extractor is followed by an extract separator in which the dye extract is separated from the extraction gas if desired together with the entraining agent. With an optimal separation of extract in mind, the pressure in this module must differ significantly from the actual extraction pressure and should therefore according to the invention be decreased in the extract separator to 5 to 10 bar. The temperature should be set to >45° C. The said changes in the extract separator can be carried out concurrently, but it is also possible to select the most favourable processing procedure for each case. The aim of this procedure is to achieve a clear gas phase separation which can be used to separate the solvent from the extract containing entraining agent.

Subsequently the separated extract containing entraining agent is withdrawn and the dye is preferably crystallized from the extract by appropriate cooling.

In a preferred embodiment of the present process the accompanying fatty substances are pre-extracted with the compressed gas(mixture) without addition of entraining agent in which the triglyceride fractions are almost completely, the carotenoid dyes, however, only partially separated. The dye extraction is subsequently completed with addition of the entraining agent by which means an extract is obtained with strong enrichment of dyes.

With a view to providing economically and ecologically sensible processes, the extraction process according to the invention is usually based on a cyclic process. In this way the extraction gas as well as the entraining agent are recovered and used again in the process.

The examples stated in the following further elucidate the described advantages of the process according to the invention.

EXAMPLE 1

Carotenoid Extraction of Plant Starting Material Without Entraining Agent 1 kg compressed propane was passed through 200 g of a commercial sweet paprika powder (carotenoid content: 0.34% by weight, water content: 11% by weight) at 20 bar and 45° C. Subsequently 22 g of a deep-red oil was collected in an extraction separator at 8 bar and 50° C. The carotenoid content in the extraction residue (178 g) was determined as 0.08% by weight. The extraction yield was thus 71% by weight relative to the total carotenoid content in the starting material after dye crystallization.

EXAMPLE 2

Carotenoid Extraction of the Fermentation Residue Using Acetone as the Entraining Agent 200 g dry fermentation residue of a fungi from the Zygomycetes class that produces carotenoid (content of carotenoid: 5.4% by weight, water content: 7% by weight) was first extracted with 1 kg compressed propane at 30 bar and 70° C. Subsequently a further 1.5 kg propane was passed through the extraction autoclave while additionally feeding in acetone (25% by weight in relation to propane). The extraction residue was subsequently re-extracted with 0.5 kg propane in order to remove the entraining agent from the residue. The corresponding extracts were collected together in the extract separator at 6 bar and 50° C. After withdrawal from the extract separator, the acetone was removed by distillation to obtain 134 g of a deep-red extract from which β-carotene was crystallized. The determination of total carotenoid in the extraction residue (66 g) yielded 2.2% by weight. The extraction yield of carotenoids was thus 86% relative to the content of the starting material.

EXAMPLE 3

Carotenoid Extraction of the Fermentation Residue Using Ethyl Acetate as the Entraining Agent 200 g of the fermentation residue from example 2 was extracted under the conditions stated there using ethyl acetate as the entraining agent instead of acetone (25% by weight in relation to propane). After removing the entraining agent from the collected extracts, 120 g of a deep-red oil was isolated. The total carotenoid content in the extraction residue (80 g) was 3.2% by weight. The extraction yield of carotenoid after the crystallization step was 69% relative to the content of the starting material.

EXAMPLE 4

Carotenoid Extraction of the Fermentation Residue Using Ethanol as the Entraining Agent 200 g of the fermentation residue from example 2 was extracted under the conditions stated there using 20% by weight ethanol (99.8%) as the entraining agent instead of acetone. After removing the ethanol from the collected extracts by distillation, 113 g of a deep-red oil was isolated. The total content of carotenoid in the extraction residue (87 g) was 4% by weight. The extraction yield of carotenoid after crystallization of the dye was 60% relative to the content of the starting material.

EXAMPLE 5

Carotenoid Extraction of Plant Starting Material Using Acetone as the Entraining Agent 200 g dry blossoms of Tagetes patula (total content of carotenoid: 4.0% by weight; water content: 8% by weight) was extracted with 0.6 kg compressed propane at 35 bar and 75° C. Using the same conditions 1 kg propane with acetone as the entraining agent (15% by weight relative to propane) was afterwards passed through the extraction autoclave and it was subsequently re-extracted with 0.5 kg propane without addition of entraining agent. After removing the collected extracts from the extract separator which was operated at 6 bar and 45° C., 29 g of an intensively coloured oily extract could be isolated after removing the entraining agent by distillation. 0.9% by weight total carotenoids was determined spectrophotometrically at 450 nm in the extraction residue (171 g). The extraction yield of carotenoid was 80% relative to the starting material.

EXAMPLE 6

Carotenoid Extraction of the Fermentation Residue Using Butane and Acetone as the Entraining Agent 200 g dry fermentation residue of a fungi of the Zygomycetes class that produces carotenoid (content of carotenoid: 5.4% by weight, water content: 7% by weight) was first extracted with 1 kg compressed butane (50% n-butane, 50% i-butane) at 13 bar and 70° C. Subsequently a further 1.5 kg extraction gas was passed through the extraction autoclave while additionally feeding in acetone (25% by weight in relation to butane). The extraction residue was subsequently extracted with 0.5 kg pure extraction gas. The respective extracts were collected together in an extract separator at 4 bar and 50° C. After withdrawal from the extract separator the acetone was removed by distillation to obtain 140 g of a deep-red extract from which β-carotene was crystallized. The determination of total carotenoid in the extraction residue (60 g) yielded 2.1% by weight. The extraction yield of carotenoids was thus about 85% relative to the content of starting material.

It will be understood that the specification and examples are illustrative but not limitative of the present invention and that other embodiments within the spirit and scope of the inventions will suggest themselves to those skilled in the art.

We claim:

1. A process for the extraction of a carotenoid dye from a natural starting material comprising:
   providing a pre-dried natural starting material;
   extracting the pre-dried natural starting material with a compressed gas selected from the group consisting of compressed propane, compressed butane, and mixtures thereof in order to obtain an extract, at a temperature of from 20° to 90° C. and a pressure of from 10 to 200 bar.

2. The process of claim 1 wherein the water content of the pre-dried natural starting material is <80 wt.-%.

3. The process of claim 2 wherein the water content of the pre-dried natural starting material is <50 wt.-%.

4. The process of claim 1 wherein the extraction is carried out at a temperature of from 50° to 90° C.

5. The process of claim 1 wherein the extraction is carried out at a pressure of from 15 to 40 bars.

6. The process of claim 1 wherein the extract is separated by at least one method selected from reducing the pressure to 5 to 10 bars, increasing the temperature to >45° C., and combinations thereof.

7. The process of claim 1 further comprising separating the extract.

8. The process of claim 7 wherein the separated extract is cooled and the carotenoid dye is crystallized.

9. The process of claim 2 wherein the water content of said pre-dried natural starting material is less than 10 wt.-%.

10. The process of claim 1 comprising conducting the extraction in the presence of an organic entraining agent.

11. The process of claim 10 wherein said organic entraining agent is selected from the group consisting of acetone, ethyl acetate, butyl acetate, short-chained alcohols with 1 to 5 carbon atoms, petroleum ether, and pure hydrocarbons.

12. The process of claim 11 wherein the organic entraining agent is selected from the group consisting of methanol, ethanol, butanol, pure hydrocarbons, and hexane.

13. The process of claim 10 wherein the organic entraining agent is present at concentrations of from about 5 to 50 wt.-% relative to the total amount of said compressed gas.

14. The process of claim 13 wherein the organic entraining agent concentration is from 10 to 30 wt.-% relative to the amount of compressed gas.

15. The process of claim 10 further comprising conducting a pre-extraction with said compressed propane and/or compressed butane prior to the extraction during which the entraining agent is added.

16. The process of claim 10 wherein the water content of the pre-dried natural starting material is <50 wt.-%.

17. The process of claim 10 wherein the temperature ranges from 50° to 90° C.

18. The process of claim 10 wherein the pressure ranges from 15 to 40 bars.

* * * * *

UNITED STATES PATENT AND TRADEMARK OFFICE
CERTIFICATE OF CORRECTION

PATENT NO.    :    5,789,647

DATED    :    August 4, 1998

INVENTOR(S)    :    HEIDLAS et al.

It is certified that error appears in the above-identified patent and that said Letters Patent are hereby corrected as shown below:

In column 2, line 20, change "Of" to -- of --.

In column 2, line 24, after "However" add -- this method --.

Signed and Sealed this

Fourteenth Day of December, 1999

Attest:

Q. TODD DICKINSON

Attesting Officer

Acting Commissioner of Patents and Trademarks